(12) United States Patent
Makolin et al.

(10) Patent No.: US 6,409,883 B1
(45) Date of Patent: Jun. 25, 2002

(54) METHODS OF MAKING FIBER BUNDLES AND FIBROUS STRUCTURES

(75) Inventors: Robert J. Makolin; Emmanuelle C. Damay; Wendy L. Hamilton, all of Neenah; Patsy A. Hansen, Omro; William G. Reeves, Appleton; Heather A. Sorebo, Appleton; Fung-jou Chen, Appleton; Jeffrey D. Lindsay, Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/548,117

(22) Filed: Apr. 12, 2000

Related U.S. Application Data

(60) Provisional application No. 60/129,746, filed on Apr. 16, 1999.

(51) Int. Cl.$^7$ ................................................ D21C 1/10
(52) U.S. Cl. ................................ 162/52; 162/9; 162/56; 162/18; 162/28; 162/111; 162/112; 428/283
(58) Field of Search ................................ 162/52, 9, 56, 162/18, 28, 111, 112; 428/283

(56) References Cited

U.S. PATENT DOCUMENTS

| | | |
|---|---|---|
| 3,089,824 A | 5/1963 | Wurster |
| 3,117,027 A | 1/1964 | Lindlof et al. |
| 3,156,242 A | 11/1964 | Crowe, Jr. |
| 3,196,827 A | 7/1965 | Wurster et al. |
| 3,241,520 A | 3/1966 | Wurster et al. |
| 3,253,944 A | 5/1966 | Wurster |
| 3,341,394 A | 9/1967 | Kinney |
| 3,395,708 A | 8/1968 | Hervey et al. |
| 3,502,763 A | 3/1970 | Hartmann |

(List continued on next page.)

FOREIGN PATENT DOCUMENTS

| | | |
|---|---|---|
| CA | 884608 | 11/1971 |
| CA | 2241820 | 2/1999 |
| DE | 1 907 914 | 10/1969 |
| EP | 0 009 977 A1 | 4/1980 |
| EP | 0 339 461 A1 | 11/1989 |
| EP | 0 458 657 A1 | 11/1991 |
| EP | 0 483 730 A1 | 5/1992 |
| EP | 0 335 253 B1 | 3/1993 |
| EP | 0 572 033 A2 | 12/1993 |
| EP | 0 381 087 B1 | 3/1994 |
| EP | 0 598 413 A1 | 5/1994 |
| EP | 0 612 233 B1 | 4/1996 |

(List continued on next page.)

OTHER PUBLICATIONS

American Society for Testing Materials (ASTM) Designation: D 1921–89, "Standard Test Methods for Particle Size (Sieve Analysis) of Plastic Materials," pp. 493–496, published Aug. 1989.

American Society for Testing Materials (ASTM) Designation: D 6128–97, "Standard Shear Testing Method for Bulk Solids Using the Jenike Shear Cell," pp. 1109–1126, published Oct. 1998.

(List continued on next page.)

Primary Examiner—Stanley S. Silverman
Assistant Examiner—Mark Halpern
(74) Attorney, Agent, or Firm—Thomas M. Parker

(57) ABSTRACT

A method of making fiber bundles and fibrous structures. The efficacy of a fiber bundle in handling complex fluids may be improved by subjecting an aqueous suspension of fibers at high consistency to elevated energy input with sufficient working of the fibers. The fibrous structures prepared according to the methods herein include at least one fiber bundle and at least one debonding agent. The fiber bundle includes at least one particulate material consisting essentially of entangled fibers.

31 Claims, 6 Drawing Sheets

U.S. PATENT DOCUMENTS

| | | |
|---|---|---|
| 3,542,615 A | 11/1970 | Dobo et al. |
| 3,554,862 A | 1/1971 | Hervey et al. |
| 3,556,932 A | 1/1971 | Coscia et al. |
| 3,556,933 A | 1/1971 | Williams et al. |
| 3,585,104 A | 6/1971 | Kleinert |
| 3,677,886 A | 7/1972 | Forssblad et al. |
| 3,692,618 A | 9/1972 | Dorschner et al. |
| 3,700,623 A | 10/1972 | Keim |
| 3,772,076 A | 11/1973 | Keim |
| 3,802,817 A | 4/1974 | Matsuki et al. |
| 3,836,336 A | 9/1974 | Yasui et al. |
| 3,849,241 A | 11/1974 | Butin et al. |
| 3,881,489 A | 5/1975 | Hartwell |
| 3,885,158 A | 5/1975 | Flutie et al. |
| 3,899,388 A | 8/1975 | Petrovich et al. |
| 3,909,009 A | 9/1975 | Cvetko et al. |
| 3,972,855 A | 8/1976 | Martinsson et al. |
| 3,989,867 A | 11/1976 | Sisson |
| 4,015,604 A | 4/1977 | Csillag |
| 4,055,180 A | 10/1977 | Karami |
| 4,076,663 A | 2/1978 | Masuda et al. |
| 4,100,324 A | 7/1978 | Anderson et al. |
| 4,129,528 A | 12/1978 | Petrovich et al. |
| 4,144,080 A | 3/1979 | McCorsley, III |
| 4,144,122 A | 3/1979 | Emanuelsson et al. |
| 4,145,532 A | 3/1979 | Franks et al. |
| 4,147,586 A | 4/1979 | Petrovich et al. |
| 4,166,464 A | 9/1979 | Korpman |
| 4,169,699 A | 10/1979 | Werner |
| 4,222,921 A | 9/1980 | Van Eenam |
| 4,247,362 A | 1/1981 | Williams |
| 4,254,179 A | 3/1981 | Carson, III et al. |
| 4,258,455 A | 3/1981 | Werner |
| 4,260,443 A | 4/1981 | Lindsay et al. |
| 4,271,412 A | 6/1981 | Austin |
| 4,278,088 A | 7/1981 | Reeves et al. |
| 4,303,471 A | 12/1981 | Laursen |
| 4,307,143 A | 12/1981 | Meitner |
| 4,335,722 A | 6/1982 | Jackson |
| 4,340,560 A | 7/1982 | Migeon |
| 4,341,215 A | 7/1982 | Eldridge |
| 4,342,314 A | 8/1982 | Radel et al. |
| 4,351,699 A | 9/1982 | Osborn, III |
| 4,366,111 A | 12/1982 | Dinius et al. |
| 4,397,644 A | 8/1983 | Matthews et al. |
| 4,410,441 A | 10/1983 | Davies et al. |
| 4,432,833 A | 2/1984 | Breese |
| 4,463,045 A | 7/1984 | Ahr et al. |
| 4,476,180 A | 10/1984 | Wnuk |
| 4,476,323 A | 10/1984 | Hellsten et al. |
| 4,482,429 A | 11/1984 | Klowak |
| 4,522,967 A | 6/1985 | Sheldon et al. |
| 4,543,098 A | 9/1985 | Wolfe et al. |
| 4,560,527 A | 12/1985 | Harke et al. |
| 4,571,924 A | 2/1986 | Bahrani |
| 4,573,986 A | 3/1986 | Minetola et al. |
| 4,578,070 A | 3/1986 | Holtman |
| 4,579,943 A | 4/1986 | Kamide et al. |
| 4,594,130 A | 6/1986 | Chang et al. |
| 4,619,862 A | 10/1986 | Sokolowski et al. |
| 4,621,011 A | 11/1986 | Fleischer et al. |
| 4,650,481 A | 3/1987 | O'Connor et al. |
| 4,654,039 A | 3/1987 | Brandt et al. |
| 4,654,161 A | 3/1987 | Kollmeier et al. |
| 4,675,394 A | 6/1987 | Solarek et al. |
| 4,681,793 A | 7/1987 | Linman et al. |
| 4,707,398 A | 11/1987 | Boggs |
| 4,715,918 A | 12/1987 | Lang |
| 4,717,498 A | 1/1988 | Maxon |
| 4,734,478 A | 3/1988 | Tsubakimoto et al. |
| 4,793,898 A | 12/1988 | Laamanen et al. |
| 4,813,948 A | 3/1989 | Insley |
| 4,824,901 A | 4/1989 | Alexander et al. |
| 4,834,739 A | 5/1989 | Linker, III et al. |
| RE32,957 E | 6/1989 | Elias |
| 4,879,170 A | 11/1989 | Radwanski et al. |
| 4,892,535 A | 1/1990 | Bjornberg et al. |
| 4,917,697 A | 4/1990 | Osborn, III et al. |
| 4,921,645 A | 5/1990 | Insley |
| 4,946,527 A | 8/1990 | Battrell |
| 4,950,264 A | 8/1990 | Osborn, III |
| 4,960,845 A | 10/1990 | O'Lenick, Jr. |
| 4,981,557 A | 1/1991 | Bjorkquist |
| 4,994,053 A | 2/1991 | Lang |
| 5,002,814 A | 3/1991 | Knack et al. |
| 5,006,116 A | 4/1991 | Alikhan et al. |
| 5,008,344 A | 4/1991 | Bjorkquist |
| 5,009,653 A | 4/1991 | Osborn, III |
| 5,011,480 A | 4/1991 | Gossens et al. |
| 5,013,309 A | 5/1991 | Baigas, Jr. et al. |
| 5,030,314 A | 7/1991 | Lang |
| 5,047,020 A | 9/1991 | Hsu |
| 5,058,247 A | 10/1991 | Thomas et al. |
| 5,070,168 A | 12/1991 | O'Lenick, Jr. |
| 5,070,171 A | 12/1991 | O'Lenick, Jr. |
| 5,073,619 A | 12/1991 | O'Lenick, Jr. |
| 5,085,736 A | 2/1992 | Bjorkquist |
| 5,098,979 A | 3/1992 | O'Lenick, Jr. |
| 5,116,563 A | 5/1992 | Thomas et al. |
| 5,120,812 A | 6/1992 | O'Lenick, Jr. et al. |
| 5,135,294 A | 8/1992 | Ohshima et al. |
| 5,147,343 A * | 9/1992 | Kellenberger |
| 5,149,765 A * | 9/1992 | O'Lenick, Jr. |
| 5,150,707 A * | 9/1992 | Anderson |
| 5,175,046 A * | 12/1992 | Nguyen |
| 5,188,625 A * | 2/1993 | Van Iten et al. |
| 5,190,563 A * | 3/1993 | Herron et al. |
| 5,196,499 A * | 3/1993 | O'Lenick, Jr. |
| 5,225,047 A * | 7/1993 | Graef et al. |
| 5,237,035 A * | 8/1993 | O'Lenick, Jr. et al. |
| 5,248,309 A * | 9/1993 | Serbiak et al. |
| 5,253,815 A * | 10/1993 | Bowns et al. |
| 5,268,213 A * | 12/1993 | Murakami et al. |
| 5,280,099 A * | 1/1994 | Imperante et al. |
| 5,296,434 A * | 3/1994 | Karl et al. |
| 5,300,055 A * | 4/1994 | Buell |
| 5,300,358 A * | 4/1994 | Evers |
| 5,300,666 A * | 4/1994 | Imperante et al. |
| 5,308,665 A * | 5/1994 | Sadek et al. |
| 5,316,601 A * | 5/1994 | Hebbard et al. |
| 5,324,278 A * | 6/1994 | Visscher et al. |
| 5,324,823 A * | 6/1994 | Asakawa et al. |
| 5,348,620 A * | 9/1994 | Hermans et al. |
| 5,350,624 A * | 9/1994 | Georger et al. |
| H1377 H | 11/1994 | Perry |
| 5,366,591 A * | 11/1994 | Jewell |
| 5,399,412 A * | 3/1995 | Sudall et al. |
| 5,405,342 A * | 4/1995 | Roessler et al. |
| 5,407,581 A * | 4/1995 | Onodera et al. |
| 5,423,787 A * | 6/1995 | Kjellberg |
| 5,429,686 A | 7/1995 | Chiu et al. |
| 5,436,066 A | 7/1995 | Chen |
| 5,447,677 A | 9/1995 | Griffoul et al. |
| 5,459,980 A | 10/1995 | Kenney et al. |
| 5,476,711 A | 12/1995 | Hebbard et al. |
| 5,501,768 A | 3/1996 | Hermans et al. |
| 5,505,720 A | 4/1996 | Walters et al. |
| 5,509,913 A | 4/1996 | Yeo |
| 5,509,914 A | 4/1996 | Osborn, III |
| 5,520,869 A | 5/1996 | Taylor |
| 5,532,311 A | 7/1996 | Sirvio et al. |

| | | |
|---|---|---|
| 5,533,991 A | 7/1996 | Kirby et al. |
| 5,595,628 A | 1/1997 | Gordon et al. |
| 5,601,542 A | 2/1997 | Melius et al. |
| H1639 H | 3/1997 | Crainic |
| 5,607,551 A | 3/1997 | Farrington, Jr. et al. |
| 5,611,790 A | 3/1997 | Osborn, III et al. |
| 5,611,932 A | 3/1997 | Lee et al. |
| 5,649,916 A | 7/1997 | DiPalma et al. |
| 5,672,248 A | 9/1997 | Wendt et al. |
| 5,679,146 A | 10/1997 | Kalt et al. |
| 5,692,939 A | 12/1997 | DesMarais |
| 5,698,151 A | 12/1997 | Zikeli et al. |
| 5,702,378 A | 12/1997 | Widlund et al. |
| 5,711,970 A | 1/1998 | Lau et al. |
| 5,718,802 A | 2/1998 | Collier et al. |
| 5,725,821 A | 3/1998 | Gannon et al. |
| 5,728,082 A | 3/1998 | Gustafsson et al. |
| 5,763,331 A | 6/1998 | Demhartner |
| 5,772,845 A | 6/1998 | Farrington, Jr. et al. |
| 5,795,377 A | 8/1998 | Tanner et al. |
| 5,795,921 A | 8/1998 | Dyer et al. |
| 5,800,417 A | 9/1998 | Goerg-Wood et al. |
| 5,817,079 A | 10/1998 | Bergquist et al. |
| 5,824,004 A | 10/1998 | Osborn, III et al. |
| 5,830,543 A | 11/1998 | Miyake et al. |
| 5,837,184 A | 11/1998 | Firgo et al. |
| 5,843,852 A | 12/1998 | Dutkiewicz et al. |
| 5,851,648 A | 12/1998 | Stone et al. |
| 5,858,021 A | 1/1999 | Sun et al. |
| 5,866,242 A | 2/1999 | Tan et al. |
| 5,879,962 A | 3/1999 | DePuydt et al. |
| 5,883,231 A | 3/1999 | Achter et al. |
| 5,935,383 A | 8/1999 | Sun et al. |
| 5,990,377 A | 11/1999 | Chen et al. |

FOREIGN PATENT DOCUMENTS

| | | |
|---|---|---|
| EP | 0 568 404 B1 | 12/1997 |
| EP | 0 858 792 A2 | 8/1998 |
| EP | 0 608 460 B1 | 9/1998 |
| EP | 0 862 904 A2 | 9/1998 |
| EP | 0 893 517 A2 | 1/1999 |
| GB | 1 546 877 | 5/1979 |
| WO | WO 95/03019 A1 | 2/1995 |
| WO | WO 95/19191 A1 | 7/1995 |
| WO | WO 96/29967 A1 | 10/1996 |
| WO | WO 98/24389 A1 | 6/1998 |
| WO | WO 98/29074 A1 | 7/1998 |
| WO | WO 98/43684 A1 | 10/1998 |
| WO | WO 98/51250 A1 | 11/1998 |
| WO | WO 99/02114 A1 | 1/1999 |
| WO | WO 99/61518 A1 | 12/1999 |
| WO | WO 00/19955 A2 | 4/2000 |
| WO | WO 00/19956 A1 | 4/2000 |
| ZA | 98/2605 | 3/1998 |

OTHER PUBLICATIONS

TAPPI Provisional Method T 270 pm–88, "Flake Content of Pulp," published by the TAPPI Press, Atlanta, Georgia, 1988, pp. 1–2.

Ahlstrom Machinery Group, "MDR® Kneader," Internet web page, "http://ahlstrom.fi/recycledfiberprocessing/MDR.htm," viewed and printed Mar. 15, 2000, pp. 1–2.

Processall, Inc., "The Development and Use of Fluidized Bed Plow Mixers," Internet web page, "http://www.processall.com/developm.htm," viewed and printed Mar. 26, 1999, pp. 1–5.

Processall, Inc., "Processall U–Max Dryer," Internet web page, "http://processall.com/dryer.htm," viewed and printed Mar. 26, 1999, 1 page.

Processall, Inc., "Processall U–Max Rotary Vacuum Dryers," Internet web page, "http://processall.com/prod02.htm," viewed and printed Mar. 26, 1999, 1 page.

Swenson Process Equipment, "Flash Dryer," Internet web page, "http://www.swenson–equip.com/flashdryer.html", viewed and printed Mar. 26, 1999, with listed update of Mar. 30, 1998, 1 page.

Swenson Process Equipment, "Fluid Bed Dryer," Internet web page, "http://www.swenson–equip.com/fluidbed.html", viewed and printed Mar. 26, 1999, with listed update of Mar. 30, 1998, pp. 1–2.

Swenson Process Equipment, "Rotary Dryer," Internet web page, "http://www.swenson–equip.com/rotary.html", viewed and printed Mar. 26, 1999, with listed update date of Mar. 30, 1998, pp. 1–2.

Austin, L.G. et al., "Size Reduction of Solids: Crushing and Grinding Equipment," Chapter 12 in *Handbook of Powder Science and Technology*, 2nd edition, Chapman & Hall, New York, 1997, pp. 586–634.

Carson, John W. et al., "Characterize Bulk Solids to Ensure Smooth Flow," *Chemical Engineering*, vol. 101, No. 4, Apr. 1994, pp. 78–82, 84, 86, 88, 90.

De Jong, J.A.H. et al., "Properly Determine Powder Plowability to Maximize Plant Output," *Chemical Engineering Progress*, vol. 95, No. 4, Apr. 1999, pp. 25–34.

Disapio, Alfred J. et al., "Microporous Macrobeads Provide New Opportunities in Skin Care," *Soap & Cosmetics*, vol. 75, No. 2, Feb. 1999, pp. 42–44, 46–47.

Hostetter, David W., "Comparing Kneading and Disk Dispersion," *PaperAge*, Nov. 1995, p. 16.

Kaye, Brian H., "Mixing of Powders," Chapter 11 in *Handbook of Powder Science & Technology*, 2nd edition, Chapman & Hall, New York, 1997, pp. 568–585.

Main, Steve et al., "Retention Aids for High–Speed Paper Machines," *Tappi Journal*, vol. 82, No. 4, Apr. 1999, pp. 78–84.

Neumann, A.W., and R.J. Good, "Techniques of Measuring Contact Angles," Chapter 2 of *Surface and Colloid Science*, vol. 11, Experimental Methods, edited by R.J. Good and R.R. Stromberg, Plenum Press, 1979, pp. 31–91.

O'Lenick, Jr., Anthony J. et al., "Silicone Compounds: Not Just Oil Phases Anymore," Soap/Cosmetics/Chemical Specialities, Jun. 1998, pp. 55–57.

Rahn, K. et al., "New Cellulosic Polymers By Subsequent Modification of 2,3–Dialdehyde Cellulose," *Cellulose Chemistry and Technology*, vol. 32, 1998, pp. 173–183.

Renner, Alfred, "High Specific Surface Area Condensation Polymers of Urea and Formaldehyde," *Die Makromelokulare Chemie*, 149, No. 3680, 1971, pp. 1–27.

Shinohara, Kunio, "Fundamental and Rheological Properties of Powders," Chapter 4 in *Handbook of Powder Science & Technology*, 2nd edition, Chapman & Hall, New York, 1997, pp. 96–145.

\* cited by examiner

FIG. 8
FIG. 9

# METHODS OF MAKING FIBER BUNDLES AND FIBROUS STRUCTURES

This application claims benefit of Provisional Application Ser. No. 60/129,746 filed Apr. 16, 1999.

BACKGROUND

The present invention relates to methods of making fiber bundles suitable for use in absorbent structures and disposable absorbent articles. More particularly, the present invention relates to methods of making fiber bundles that exhibit an improved efficacy in the handling of complex fluids.

The use of fiber bundles in disposable absorbent articles is known. Such fiber bundles are generally employed on a somewhat limited basis in disposable personal care absorbent articles such as feminine hygiene products, diapers, training pants, incontinence products and the like. However, a more widespread use of such fiber bundles in absorbent structures and disposable absorbent articles has been somewhat confined by the limited efficacy of the fiber bundles in the handling of complex fluids. Thus, it would be desirable to improve the efficacy of the fiber bundles in the handling of complex fluids, potentially resulting in the broadened use of such fiber bundles in absorbent structures and disposable absorbent articles.

SUMMARY

The present inventors have recognized the difficulties and problems inherent in the prior art and in response thereto conducted intensive research into a method of preparing fiber bundles that exhibit an improved efficacy in the handling of complex fluids. While conducting such research, the inventors surprisingly found that by incorporating a debonding agent the fiber bundles of the present invention exhibited an improved efficacy in the handling of complex fluids. The inventors also found that by increasing the energy input into a disperser, fiber bundles of desired particles sizes were prepared.

In one embodiment, an aqueous suspension of fibers is formed having an inlet consistency of at least about 20 weight percent. The aqueous suspension is then passed through a disperser with an energy input of at least about 90 kW-h/T of dry fiber to form fiber bundles that are extruded from the disperser.

In another embodiment, an aqueous suspension of fibers is formed having an inlet consistency of at least about 20 weight percent. A debonding agent is added to the aqueous suspension. Subsequent to adding the debonding agent, the aqueous suspension is passed through a disperser with an energy input of at least about 90 kW-h/T of dry fiber to form fibrous structures that are extruded from the disperser.

In yet another embodiment, an aqueous suspension of fibers is formed having an inlet consistency of at least about 20 weight percent. The aqueous suspension is passed through a disperser with an energy input of at least about 90 kW-h/T of dry fiber to form fiber bundles that are extruded from the disperser. A debonding agent is added to the extruded fiber bundles to form fibrous structures.

In still another embodiment, an aqueous suspension of fibers is formed having an inlet consistency of at least about 20 weight percent. The aqueous suspension is passed through a disperser with an energy input of at least about 90 kW-h/T of dry fiber. A debonding agent is added to the aqueous suspension as it passes through the disperser to form fibrous structures that are extruded from the disperser.

In a further embodiment, an aqueous suspension of fibers is formed having an inlet consistency of at least about 20 weight percent. The aqueous suspension is then passed through a disperser with an energy input of at least about 90 kW-h/T of dry fiber to form fiber bundles that are extruded from the disperser. The extruded fiber bundles are then dried. Subsequent to drying, a debonding agent is added to the extruded fibers to form fibrous structures.

DRAWINGS

FIG. 8 illustrates a flowability index.

FIG. 9 illustrates a cohesivity index.

DESCRIPTION

Figure 1:
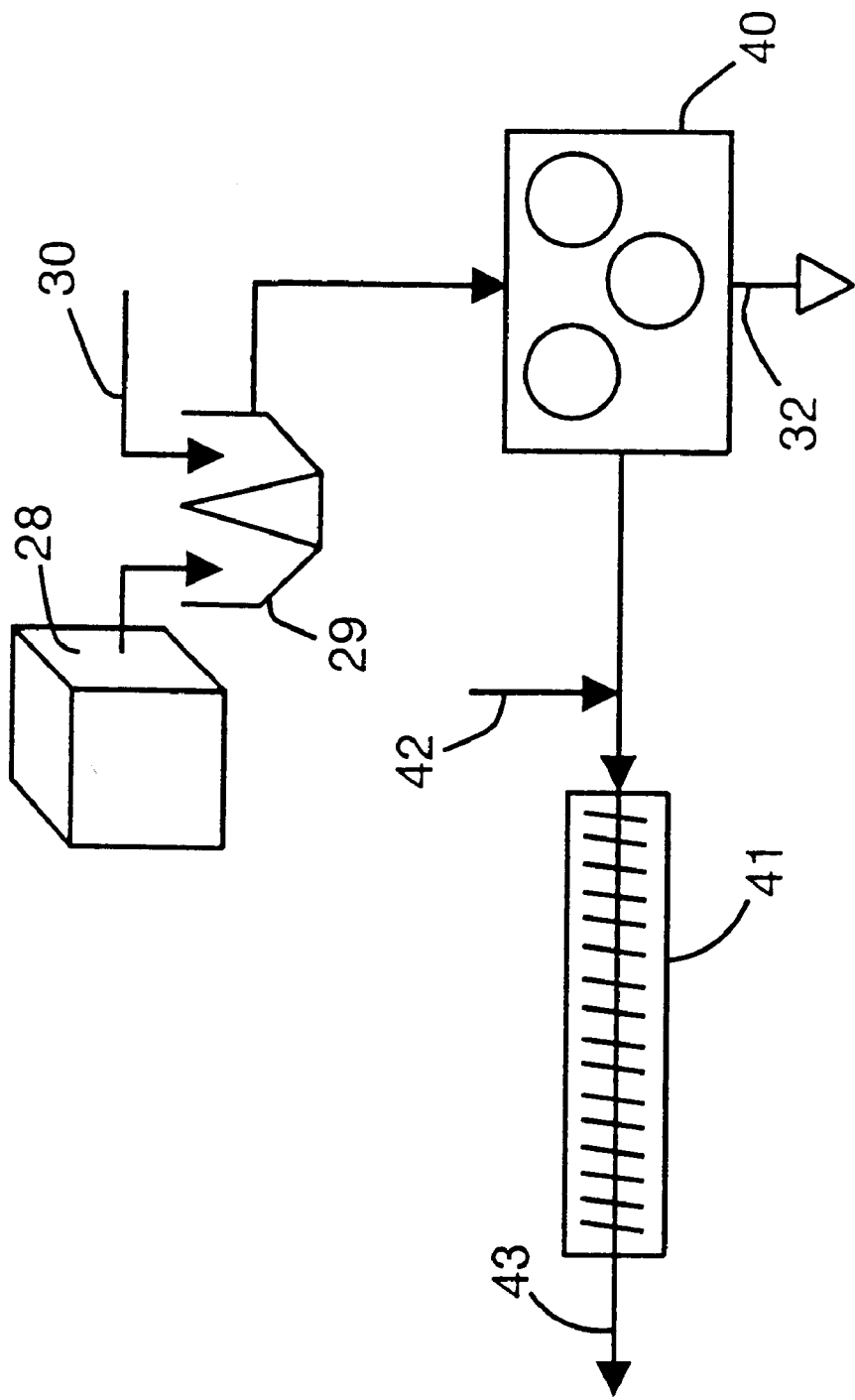
FIG. 1 illustrates a schematic process flow diagram of a process for preparing fiber bundles using a shaft disperser.

As used herein, the term "flowability" and other similar terms are intended to generally describe the ability of objects, materials, structures, particles or the like to move or flow in response to gravity and other externally applied forces.

By "particle," "particles," "particulate," "particulates" and the like, it is meant that a material is generally in the form of discrete units. The particles can include granules, pulverulents, powders or spheres. Thus, the particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for use herein. The use of "particle" or "particulate" may also describe an agglomeration including more than one particle, particulate or the like.

The term "fiber" or "fibrous" is used herein to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

As used herein, the term "fiber bundle" is meant to refer to a generally particulate material consisting essentially of entangled fibers. As such, the fiber bundle will also generally comprise capillaries or voids within the structure of the fiber bundle between the entangled fibers forming the fiber bundle. A fiber bundle may also be referred to by other terms known in the art such as "fiber nits" or "fiber flakes."

As used herein, the phrase "an otherwise substantially similar fibrous structure that does not comprise the debonding agent" and other similar phrases are intended to refer to a control fibrous structure that is prepared using substantially similar materials and a substantially similar process as compared to a fibrous structure prepared according to the present invention, except that the control fibrous structure does not include or is not prepared with one of the debonding agents described herein. As a result of not including a debonding agent, the otherwise substantially similar fibrous structure generally will not exhibit the desired improved efficacy in the handling of complex fluids as described herein when compared to the fibrous structures prepared according to the present invention.

As used herein, the phrase "complex fluid" describes a fluid generally characterized as being a viscoelastic mixture including specific components having generally inhomogeneous physical and/or chemical properties. It is the inhomogeneous properties of the specific components that challenge the efficacy of a material in the handling of complex fluids, such as, for example, blood, menses, loose passages, nasal discharges and the like. In contrast with complex fluids, simple fluids, such as, for example, urine, physiological saline, water and the like, are generally characterized as being Newtonian and including one or more components having generally homogeneous physical and/or chemical properties. As a result of having homogeneous properties, the one or more components of simple fluids behave substantially similarly during absorption or adsorption.

Although a complex fluid is generally characterized herein as including specific components having inhomogeneous properties, each specific component of a complex fluid generally has homogeneous properties. Consider for example a hypothetical complex fluid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

The term "surface" and its plural generally refer herein to the outer or the topmost boundary of an object, material, structure, particle or the like.

As used herein, the phrase "absorbent article" refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to: health care related products including ostomy products, surgical drapes, gowns, and sterilization wraps; personal care absorbent products such as feminine hygiene products (e.g., sanitary pads, pantiliners and the like) diapers, training pants, incontinence products and the like; as well as facial tissues.

Disposable absorbent articles such as, for example, many of the personal care absorbent products, typically include a fluid pervious topsheet, a liquid impervious backsheet joined to the topsheet and an absorbent core positioned between the topsheet and the backsheet. Disposable absorbent articles and components thereof, including the topsheet, backsheet, absorbent core and any individual layers of these components, generally have a body-facing surface and a garment-facing surface. As used herein, "body-facing surface" refers to that surface of the article or component which is intended to be worn toward or placed adjacent to the body of the wearer, while the "garment-facing surface" is on the opposite side and is intended to be worn toward or placed adjacent to the wearer's undergarments when the disposable absorbent article is worn.

One skilled in the art will recognize materials suitable for use as the topsheet and backsheet. Examples of materials suitable for use as the topsheet are liquid-permeable materials, such as spunbonded polypropylene or polyethylene having a basis weight of from about 15 to about 25 grams per square meter. Examples of materials suitable for use as the backsheet are liquid-pervious materials, such as polyolefin films, as well as vapor-pervious materials, such as microporous polyolefin films.

The fibrous structures prepared according to the present invention may be employed in a disposable absorbent article in the form of an absorbent structure. Such an absorbent structure may be positioned between a liquid-permeable topsheet and a backsheet attached to the topsheet. The absorbent structure in this instance may include a fibrous matrix into which, for example, the fibrous structures are dispersed such that the fibrous matrix constrains or entraps the fibrous structures.

The fibrous structures of the present invention may also be employed in a disposable absorbent article in a manner quite different from that described above. For example, an absorbent article may be constructed which consists essentially of a plurality of fibrous structures positioned between a fluid-permeable topsheet and a liquid-impermeable backsheet attached to the topsheet. When employed in such a manner, it is believed that the flowability of the fibrous structures of the present invention allow the disposable absorbent article described herein to respond to external forces such as, for example, those typically applied by the body of a woman wearing a sanitary pad or pantiliner. In order to respond to the application of such external forces, it is further desired that the fibrous structures of the present invention exhibit a flowability that is substantially similar to the flowability of an otherwise substantially similar fibrous structure that does not comprise the debonding agent. Desirably, the fibrous structures of the present invention demonstrate a flowability index of between 0 and about 7; alternatively, between 0 and about 6; alternatively, between about 1.5 and about 6; and finally, alternatively, between about 3.5 and about 5.5.

It should be noted that the disposable absorbent articles described herein may include a mixture of one or more types of fibrous structures or a mixture of at least one type of fibrous structures and at least one other particulate material. For example, a disposable absorbent article may include a first type of fibrous structure made of one or more types of suitable materials as well as a second type of fibrous structures made of one or more types of suitable materials different from those materials included in the first type of fibrous structure. In addition, a disposable absorbent article may include a mixture of at least one type of fibrous structure and at least one other particulate material such as, for example, a superabsorbent material.

As used herein, the term "equivalent particle size" and other similar terms are intended to be a measure of the equivalent diameter of a particle as if the particle was assumed to be spherically shaped. The equivalent particle size may be quantified, for example, by sieving a particle sample according to ASTM test method D-1921. Alternatively, the equivalent particle size for individual particles may be determined by an image analysis method wherein a particle sample is placed on a glass plate and a high-resolution picture is taken. From the measured area of a particle, the equivalent particle size can be calculated by assuming that the particle is circular across its cross-section. Fiber bundles prepared according to the present invention desirably have an equivalent particle size that is between about 150 and about 1,000; more desirably, between about 200 and about 850; and most desirably, between about 300 and about 600 microns.

A wide variety of natural and synthetic fibers can be employed in the preparation of the fiber bundles suitable for use in the fibrous structures prepared according to the present invention. Illustrative fibers include, but are not limited to, wood and wood products such as wood pulp fibers, cellulose or cellulose acetate flocs, cotton linter flocs and the like, inorganic fibers, synthetic fibers such as nylon flocs, rayon flocs, polyacrylonitrile fibers, and the like. It is also possible to use mixtures of one or more natural fibers, one or more synthetic fibers, or combinations of natural and synthetic fibers.

Suitable fibers are those which are wettable in nature. As used herein, the term "wettable" is meant to refer to a fiber or material which exhibits a water in air contact angle of less than 90°. In general, a wettable fiber refers to a fiber which exhibits a water in air contact angle of less than 90°, at a temperature between about 0° C. and about 100° C., and, suitably, at about room temperature.

However, nonwettable fibers can also be used. It is possible to treat the fiber surfaces by an appropriate method to render them more or less wettable. When surface-treated fibers are employed, the surface treatment is desirably nonfugitive; that is, the surface treatment desirably does not wash off the surface of the fiber with the first liquid insult or contact. For the purposes of the present invention, a surface treatment on a generally nonwettable fiber will be considered to be nonfugitive when a majority of the fibers demonstrate a water-in-air contact angle of less than 90° for three consecutive contact angle measurements, with drying between each measurement. That is, the same fiber is subjected to three separate contact angle determinations and, if all three of the contact angle determinations indicate a contact angle of water in air of less than 90°, the surface treatment on the fiber will be considered to be nonfugitive. If fugitive, the surface treatment will tend to wash off of the fiber during the first contact angle measurement, thus, exposing the nonwettable surface of the underlying fiber and will demonstrate subsequent contact angle measurements greater than 90°. Suitable wettability agents include polyalkylene glycols, such as polyethylene glycols. Typically, the wettability agent is used in an amount equivalent to less than about 5 weight percent; desirably, less than about 3 weight percent; and more desirably, less than about 2 weight percent of the total weight of the fiber being treated.

Desirably, at least the surface of the fibers or at least the surface of the fiber bundles are treated with a debonding agent. Debonding agents are generally commercially available as pulp additives, which tend to reduce fiber-to-fiber bonding in a pulp sheet, thus increasing softness. Debonding agents suitable for use in the present invention include, for example, tertiary amino compounds, quaternary amino compounds and amine oxides. Desired debonding agents carry a slight positive charge in order to enhance attachment onto negatively charged pulp fibers. Specific examples of debonding agents suitable for use in the present invention include MacKernium 516Q (a tertiary amine, commercially from MacIntyre Group Ltd., 24601 Governor's Highway, University Park, Ill. 60466 USA) and MacKernium KP (a quaternary amine, commercially from MacIntyre Group Ltd., 24601 Governor's Highway, University Park, Ill. 60466 USA). Although described herein as being somewhat cationic in nature, one skilled in the art will readily appreciate that debonding agents which tend to reduce fiber-to-fiber bonding in a pulp sheet may be cationic, anionic or nonionic in nature. Desirably, a debonding agent is present in an amount of from about 0.1 to about 10; more desirably, from about 0.3 to about 4; and, most desirably, from about 0.5 to about 2 percent by dry weight of the fiber bundles.

The flowability of the fibrous structures of the present invention may be further enhanced by including silicone compounds, silicone-based compounds, anti-static agents, softening agents, and the like. Examples of suitable silicone compounds include silicone alkylamido quaternary compounds based on dimethicone copolyol chemistry; silicone esters, including phosphate esters; dimethiconol stearate and dimethicone copolyol isostearate; silicone copolymers with polyacrylate, polyacrylamide or polysulfonic acid; silicone iethioniates; silicone carboxylates; silicone sulfates; silicone sulfosuccinates; silicone amphoterics; silicone betaines; and silicone imidazoline quats.

Fiber bundles generally occur naturally in processes for preparing fibers, such as in a pulping process, wherein some of the processed fibers become entangled. The amount of fiber bundles present in a pulp sample may be determined, for example, by the standardized TAPPI test procedure T 270 pm-88 (provisional method—1988), "Flake content of pulp." Fiber bundles, however, are generally undesirable, since the fiber bundles usually exhibit or impart properties on a final product different from those properties exhibited or imparted by unentangled fibers. In paper making, for example, fiber bundles are generally undesirable because the fiber bundles usually result in poor formation and poor surface smoothness of the paper. In addition, fiber bundles can substantially reduce the absorbency, resiliency and loft of an absorbent product. As such, any fiber bundles that survive a pulping process are generally removed from the substantially unentangled fibers by processes such as cleaning, screening, or low-consistency refining. Thus, fiber bundles may be collected as they are removed from typical fiber preparation processes. Alternatively, fiber bundles may be prepared directly by sufficiently entangling fibers in processes such as mixing or blending. Regardless of the method of preparation, the fiber bundles may be collected in either a dry or a wet state. If collected in a wet state, it may be desirable to dry the fiber bundles before use. Such drying may be accomplished by any of a number of known drying methods including, for example, air-drying, oven-drying, through-air-drying and the like. Furthermore, it may be desirable or necessary to treat the fiber bundles so as to sufficiently separate the fiber bundles.

FIG. 1 illustrates a schematic process flow diagram of a process suitable for preparing the desired fiber bundles. Shown is the paper furnish (28) to be treated being fed to a high consistency pulper (29) (Model ST6C-W, Bird Escher Wyss, Mansfield, Mass. USA) with the addition of dilution water (30) to reach a consistency of about 15 percent. Prior to being pumped out of the high consistency pulper (29), the aqueous suspension is further diluted to a consistency of about 10 percent. The aqueous suspension is then fed to a belt press (40) (Arus-Andritz Belt Filter Press Model CPF 20 inches, Andritz-Ruthner Inc., Arlington, Tex. USA) to increase the consistency to about 35 dry weight percent. The resulting aqueous suspension is then fed to a disperser (41), such as, for example, that described in detail in FIG. 2, in order to work the fibers into the desired fiber bundles. Steam (42) is optionally added to the disperser feed stream to elevate the temperature of the feed material.

The inlet temperature of the aqueous suspension initially fed into a disperser is desirably about 20° C. or greater; more desirably, about 50° C. or greater; and, most desirably, about 90° C. or greater. The inlet consistency of the aqueous suspension initially fed into a disperser desirably is high enough to provide significant fiber-to-fiber contact or working which will alter the surface properties of the treated fibers. Specifically, the inlet consistency can be at least about 20; desirably, from about 20 to about 50; more desirably, from about 25 to about 45; and, most desirably, from about 30 to about 40 dry weight percent. The consistency will be primarily dictated by the kind of disperser used to treat the fibers. For some rotating shaft dispersers, for example, there is a risk of plugging the machine at consistencies above about 40 dry weight percent. For other types of shaft dispersers, such as a BIVIS shaft disperser (commercially available from Clextral Co., Firminy Cedex, France), consistencies greater than about 50 dry weight percent can be utilized without plugging. It is desirable to utilize a consistency which is as high as possible for the particular disperser used.

While in a disperser, the amount of energy applied to the aqueous suspension also impacts the desired properties of the fiber bundles produced. Desirably, the amount of energy applied is at least about 90 kilowatt-hours per metric ton (kWh/T) of dry fiber in suspension. The amount of energy applied may, however, range as high as about 300 kWh/T of dry fiber in suspension. Generally, a suitable range of energy input is between about 90 and about 300; desirably, between about 95 and about 200; more desirably, between about 100 and 150; and, most desirably, between about 110 and about 140 kWh/ton of dry fiber in suspension.

The outlet consistency of the extruded fiber bundles is desirably from about 20 to about 75; more desirably, from about 40 to about 60; and, most desirably, from about 45 to about 55 dry weight percent. The outlet temperature of the extruded fiber bundles is greater than about 50; desirably, greater than about 80; more desirably, from about 90 to about 130; and, most desirably, from about 110 to about 115° C.

With regard to characterization of its internal structure, a suitable fiber bundle typically has a mean percent pore area of between about 30 and about 70; desirably, between about 35 and about 60; more desirably between about 40 and about 55; and, most desirably, between about 45 and 50. A fibrous structure of the present invention also desirably has an area weighted pore length of between about 100 and about 250; more desirably, between about 130 and about 210; and, most desirably, between about 150 and about 190 $\mu$m. In addition to the foregoing characterization of its internal structure, a suitable fiber bundle has a pore spacing of between 0 and about 10; desirably, between 0 and about 8; more desirably, between 0 and about 6; and, most desirably, between 0 and about 5 $\mu$m.

The fibrous structures of the present invention suitably should be able to retain a complex fluid. The ability of a fibrous structure prepared according to the present invention to retain a complex fluid is an indication of the efficacy of the fibrous structures in the handling of a complex fluid and is quantified herein as the complex fluid retention capacity. The complex fluid retention capacity is a quantification of the amount of complex fluid that a fibrous structure retains after a force has been applied. The amount of complex fluid retained is calculated as a gram per gram retention. Suitably, a fibrous structure prepared according to the present invention has a complex fluid retention capacity, as further defined hereinbelow, that is between about 20 and about 40; alternatively, between about 20 and about 38; and finally, alternatively, between about 20 and about 26 percent greater than the complex fluid retention capacity exhibited by an otherwise substantially similar fibrous structure that does not include a debonding agent.

In working the fibers within the disperser, such as by shearing and compression, it is necessary that the fibers experience substantial fiber-to-fiber contact by rubbing or shearing in addition to rubbing or shearing contact with the surfaces of the dispersers used to treat the fibers. Some compression, which means pressing the fibers into themselves, is also desirable to enhance or magnify the effect of the rubbing or shearing of the fibers. The desired fiber-to-fiber contact can in part be characterized by apparatus having a relatively high volume-to-working surface area ratio which increases the likelihood of fiber-to-fiber contact. The working surface for purposes herein is defined as that surface of the disperser which contacts the majority of the fibers passing through. For example, disc dispersers have a very low volume-to-working surface area (approximately 0.05 centimeters) because there is a relatively small volume or space between the opposed rotating discs (working surfaces). Such devices work the fibers primarily by contact between the working surfaces and the fibers. However, the dispersers particularly suitable for purposes of this invention, such as the various types of shaft dispersers, have a much higher volume-to-working surface area. Such volume-to-working surface area ratios can be about 1 centimeter or greater; desirably, about 3 centimeters or greater; and, more desirably, from about 5 to about 10 centimeters. These ratios are orders of magnitude greater than those of disc dispersers.

Once the fiber bundles are extruded in their moist state, it is desirable that they be agitated and maintained in a loose state during drying or until they are sufficiently dry in an effort to minimize the likelihood that hydrogen bonds between fiber bundles will form. Any number of commercial dryers, fluidized bed systems, and high shear dryers can be adapted to the purpose of drying fiber bundles, using principles well known to one skilled in the art. Suitably, the fiber bundles, once dried, are substantially free of clumps of multiple fiber bundles. Thus, some form of agitation during drying is generally desired. Agitation after drying to break apart clumps is less desired.

The debonding agent may be provided in the furnish prior to dispersing, during the dispersing process, or after the dispersing process. If after the dispersing process, the debonding agent may be provided to the fiber bundles before, during or after drying. A debonding agent in pure form or in aqueous solution may be applied uniformly or nonuniformly to all or a portion of either the surface of the fibers or the surface of the fiber bundles. Debonding agents may be applied by spray, by contact with a wetted surface, by trickling of a stream into a bed of fiber bundles or by any other suitable application method known to one skilled in the art. One skilled in the art will also readily appreciate that other chemical additives, such as, for example conditioners, anti-static agents, softening agents and the like, may be incorporated into the fibrous structures in a manner similar to that by which the debonding agents are incorporated into the fibrous structures.

In another process embodiment, the conversion of fibers into fiber bundles can be achieved using two or more steps of dispersing or kneading. Thus, for example, hardwood fibers or a slurry comprising hardwood fibers can be substantially curled or formed into fiber bundles in a first dispersing operation. The dispersed fibers or fiber bundles may then be dried, followed by adjustment of the moisture content to bring the consistency to at least about 20, such as from about 20 to about 30 dry weight percent. Thereafter, the fibers are again subjected to dispersing at a suitable energy input to create fiber bundles, which are then dried. Without desiring to be bound by theory, it is believed that a second dispersing step under the same or different processing conditions (e.g., different consistency, different mechanical equipment, etc.) may enhance existing desired properties or introduce new desirable properties in any resulting fibrous structure. In addition, it is believed that drying or partial drying after a first dispersing step, followed by remoistening, a second dispersing step, and final drying, may also serve to enhance existing desired properties or introduce new desirable properties in any resulting fibrous structure.

Another benefit of dispersing fiber bundles in two or more stages is that a first chemical can be added in a first dispersing step, followed by the addition of a second chemical in a second dispersing step. This can be particularly helpful when the two chemicals would give undesired reactions when added simultaneously, such as an anionic compound and a cationic compound. For example, an anionic anti-microbial compound and a cationic wet strength agent or debonding agent could be added in separate dispersing steps. Alternatively, two charged compounds can be added that would normally interfere with each other or cause precipitation.

Figure 2:
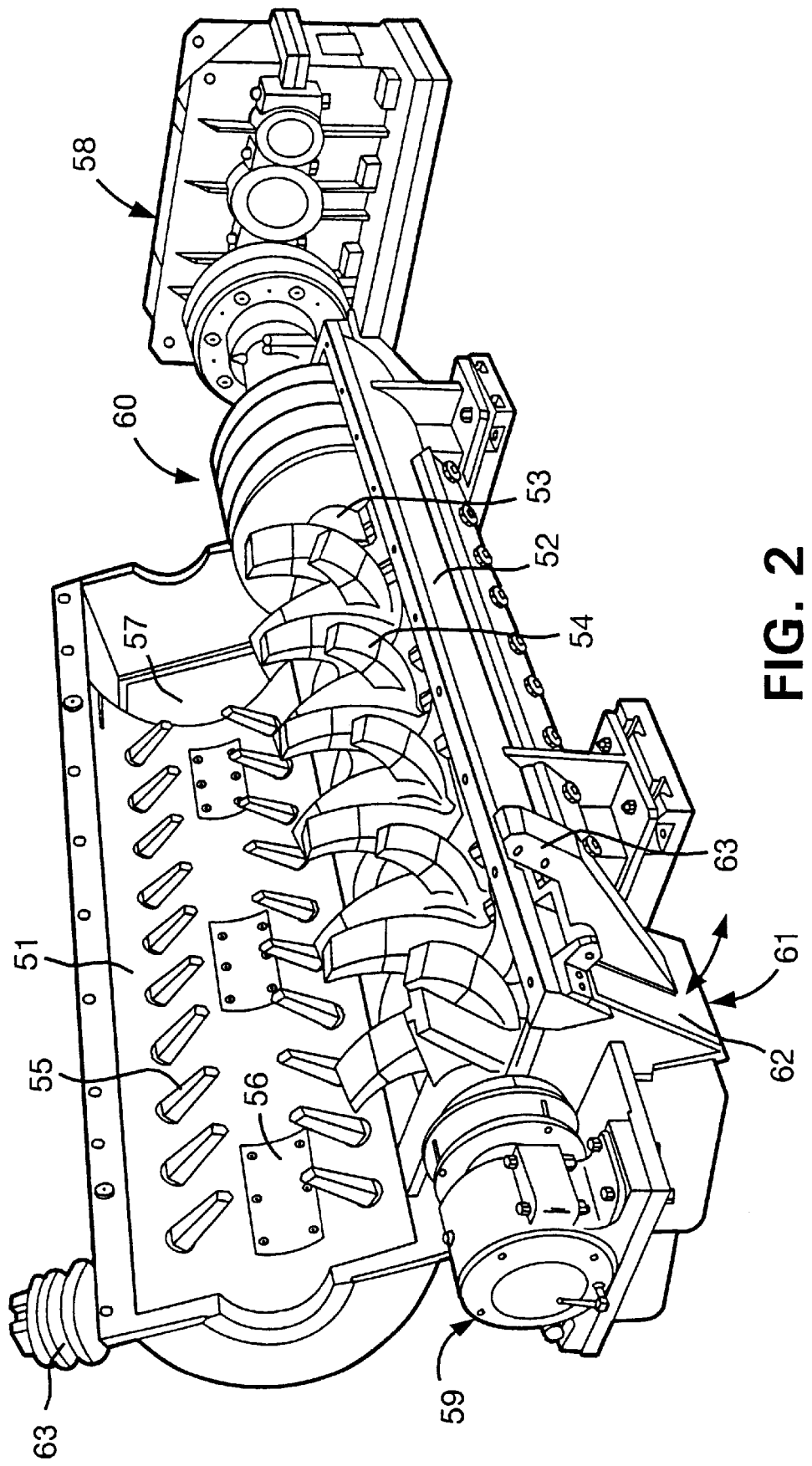
FIG. 2 illustrates a cut-away perspective view of the shaft disperser of FIG. 1.

FIG. 2 illustrates a cut-away perspective view of an apparatus suitable for treating fibers in accordance with this invention as illustrated in FIG. 1. The particular apparatus is a shaft disperser, type GR II, manufactured by Ing. S. Maule & C. S.p.A., Torino, Italy. This apparatus has a volume-to-working surface area of about 8.5 centimeters. Shown is an upper cylindrical housing (51) and a lower cylindrical housing (52) which, when closed, enclose a rotating shaft (53) having a multiplicity of arms (54). The upper cylindrical housing (51) contains two rows of knurled fingers (55) and three inspection ports (56). At one end of the upper cylindrical housing (51) is an inlet port (57). At the inlet end of the rotating shaft (53) is a drive motor (58) for turning the shaft. At the outlet end of the rotating shaft (53) is a bearing housing (59) which supports the shaft. The inlet end of the rotating shaft (53) contains a screw feed section (60) which is positioned directly below the inlet and serves to urge the feed material through the disperser. The outlet (61) of the disperser comprises a hinged flap (62) having a lever (63) which, when the disperser is closed up, is engaged by the hydraulic air bags (63) mounted on the upper cylindrical housing (51). The hydraulic air bags (63) provide controllable resistance to the rotation of the hinged flap (62) and hence provide a means of controlling the backpressure within the disperser. Increasing the backpressure increases the degree to which the fibers are worked. During operation, the knurled fingers interdigitate with the arms of the rotating shaft to work the feed material therebetween.

Figure 3:
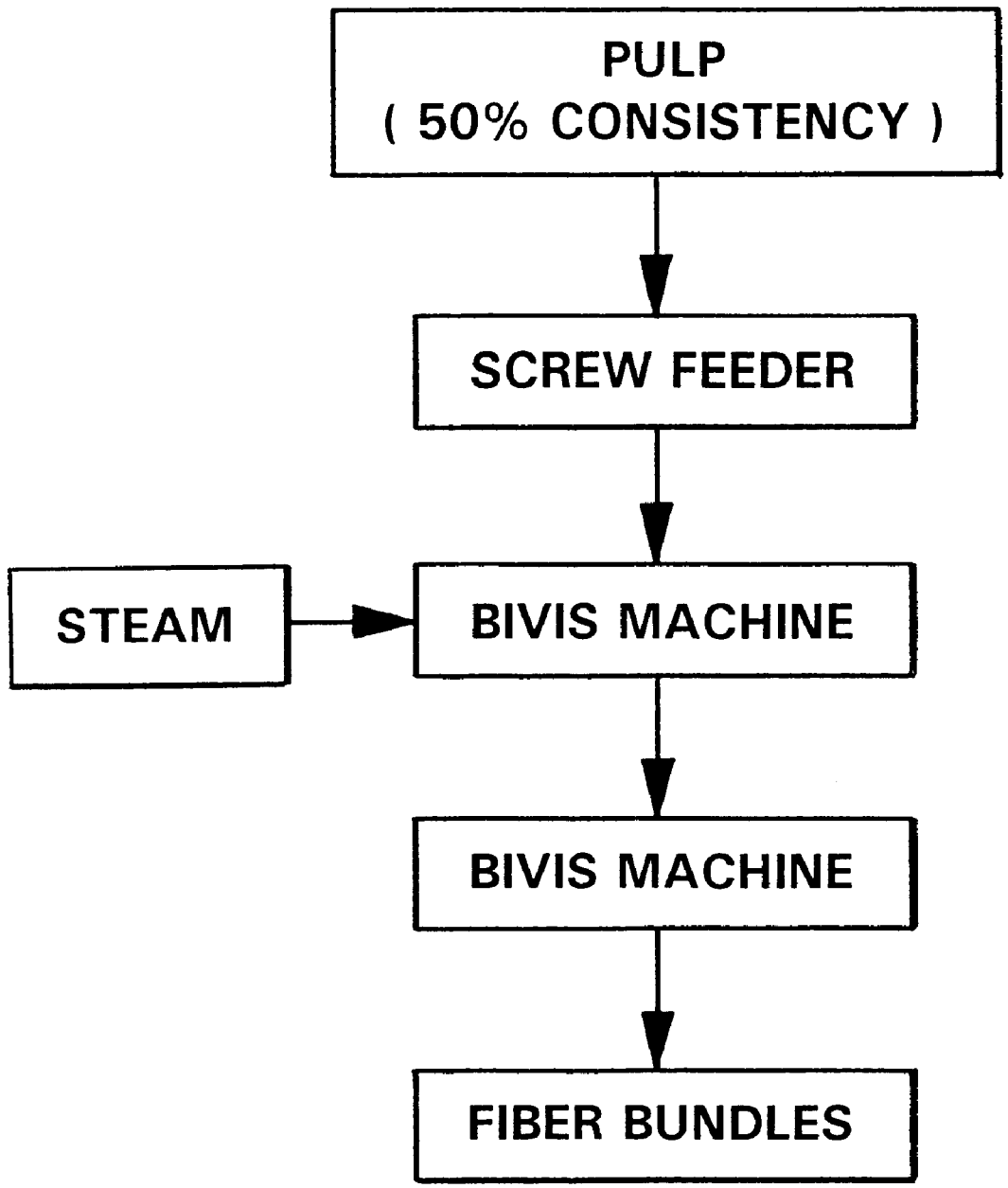
FIG. 3 illustrates an alternative schematic process flow diagram of a process for preparing fiber bundles using a pair of BIVIS shaft dispersers in series.

FIG. 3 illustrates a schematic process flow diagram of an alternative process of this invention utilizing a pair of BIVIS shaft dispersers. As illustrated, the fibrous slurry at a consistency of about 50 percent is fed to a screw feeder. The screw feeder meters the fibrous slurry to the first of two BIVIS shaft dispersers in series. Each BIVIS shaft disperser typically has three or four compression/expansion zones. Steam is injected into the first BIVIS shaft disperser to raise the temperature of the fibers to at least about 100° C. The worked pulp is transferred to the second BIVIS shaft disperser operating at approximately the same conditions as the first disperser. In an alternative process embodiment, the second BIVIS disperser may operate at conditions different than those of the first disperser.

Figure 4:
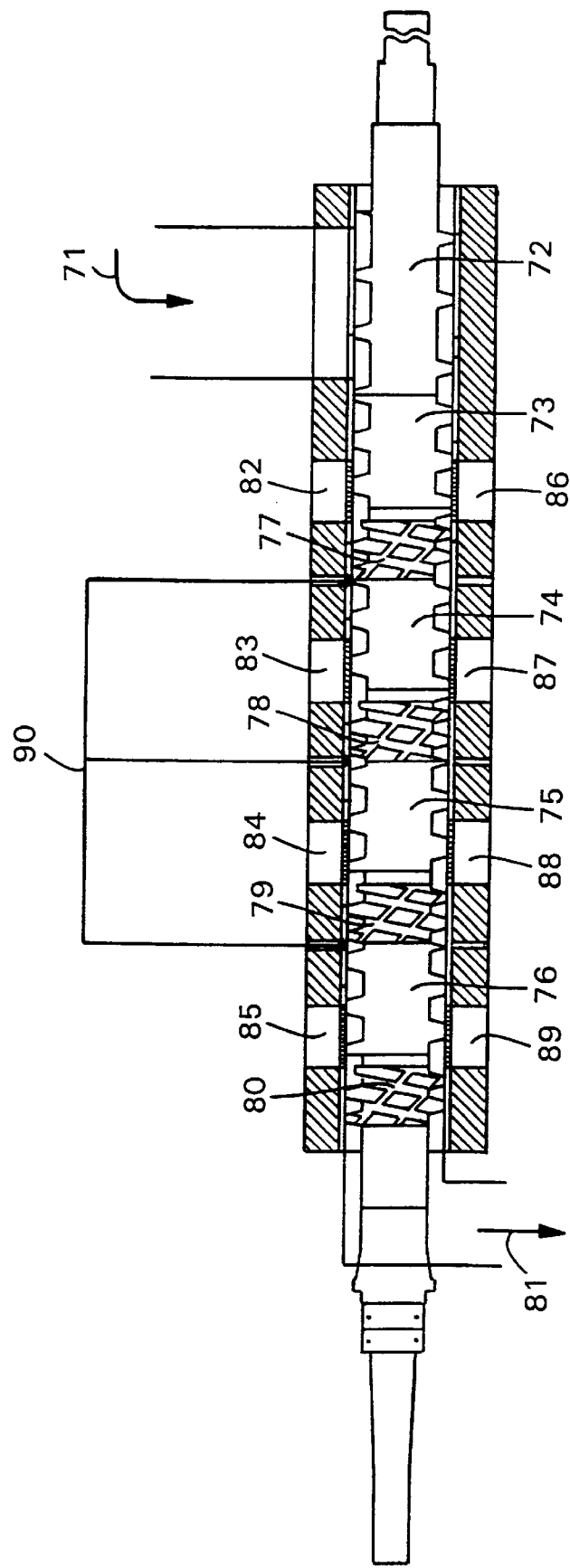
FIG. 4 illustrates a sectional view of a BIVIS shaft disperser suitable for preparing fiber bundles.

FIG. 4 illustrates a sectional elevational view of a twin screw BIVIS shaft disperser useful for purposes of this invention. Shown are the inlet (71), a short feed screw (72), forward-flighted screws (73, 74, 75 and 76), reverse-flighted screws (77, 78, 79 and 80), an outlet (81), injection ports (82, 83, 84 and 85), optional extraction ports (86, 87, 88 and 89), and thermocouples (90). In operation, a fibrous slurry is introduced into the BIVIS through the inlet (71). The fibrous slurry then encounters the short feed screw (72), which serves to introduce the fibrous slurry into the first working zone. The working zones consist of a pair of slightly overlapping screws encased in cylinders with less than 1 millimeter clearance between the screw flights and the cylinder walls. The twin screws rotate in the same direction, and at approximately the same speed. Shaft rotation transports the fibrous slurry axially through the machine. Key to the fiber property modification within the machine are the reverse-flighted screw sections which have small slots machined into the flights and are positioned periodically along the length of both screws. These reverse-flighted sections serve to reverse the flow of fibers through the machine, thereby introducing backpressure to the fibrous slurry. Thus, the stock travels forward axially until it encounters a backpressure zone. The pressure builds in this zone, but because of the slots in the reverse flights, the pressure behind is greater than the pressure ahead. In this manner, the stock is forced through the slots where it encounters the next (lower pressure) forward-flighted section of the screws. It is theorized that this compression/expansion action further enhances the modification of fiber properties. Typically, the BIVIS shaft disperser is set up to include three or four working zones. The injection ports can be used to inject debonding agents or other chemicals into each of the individual working zones. The extraction ports associated with each working zone can be used to extract liquid if desired. Although not measured, the volume-to-surface area ratio of the BIVIS shaft disperser is believed to be slightly less than that of the Maule shaft disperser.

Figure 5:
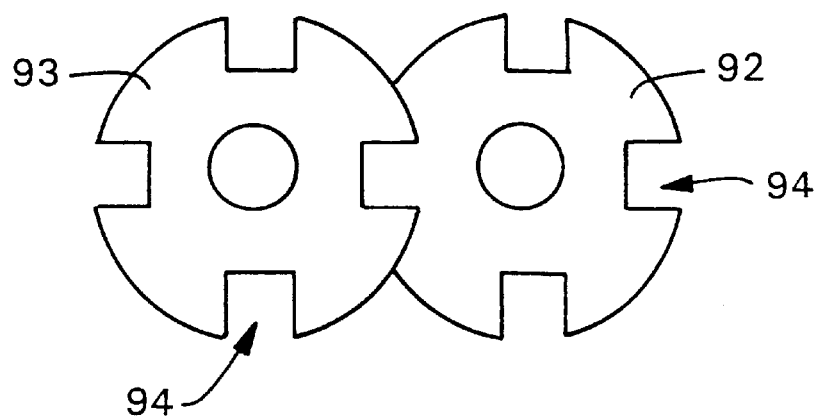
FIG. 5 illustrates a sectional view, viewed in the axial direction, of the reverse-flighted screws of a BIVIS shaft disperser, illustrating the cut-out notches in the flights.

FIG. 5 illustrates an axial view of a reverse-flighted section of the twin screws of the apparatus illustrated in FIG. 4. Illustrated are screws (92, 93), each having slots (94) machined out of their flights. As illustrated, the flights of each screw overlap.

Figure 6:
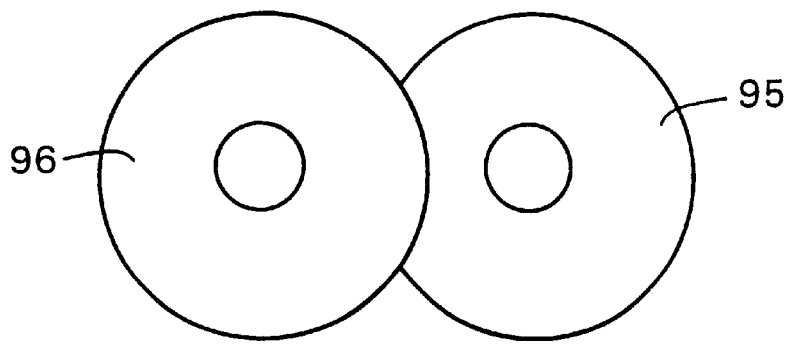
FIG. 6 illustrates a sectional view, viewed in the axial direction, of the forward flighted screws.

FIG. 6 illustrates an axial view of a forward-flighted section of the twin screws of the apparatus illustrated in FIG. 4, illustrating the overlap of the screw flights (95, 96).

Figure 7:
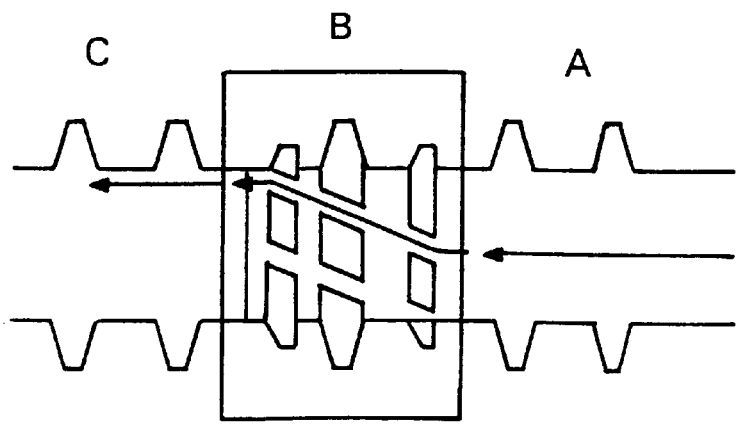
FIG. 7 illustrates a sectional view of a reverse-flighted section of a BIVIS disperser, illustrating the flow of the aqueous suspension.

FIG. 7 illustrates an expanded sectional view of a working zone of the apparatus illustrated in FIG. 4, illustrating the upstream forward-flighted screw section "A", the reverse-flighted screw section "B" and the downstream forward-flighted screw section "C.". FIG. 7 also serves to illustrate the flow of fibrous slurry (represented by the arrows) through the reverse-flighted screw section.

Although the present invention has been described in considerable detail with reference to shaft dispersers, the use of other dispersers is possible. For example, the use of disc dispersers, kneaders or other similar apparatus is possible.

Test Methods

Intake Rate and Rewet Test Method

As used herein, the Intake Rate and Rewet Test Method measures at least the following two characteristics of materials:

1. Intake rate—the amount of time, in seconds, it takes for a known amount of material to intake multiple insults of known quantities of a fluid; and
2. Rewet—the amount of fluid, in grams, that is released from the material when blotter paper is placed on top of the material and a known pressure is applied for a predetermined period of time.

Testing according to this method consisted of using a stopwatch to determine the amount of time, in seconds, required for 20 mL of material to intake multiple insults (1 or 2 mL) of fluid. A Harvard Syringe Pump is programmed to dispense 2 mL of fluid onto 20 mL of absorbent material, at which time a stopwatch is simultaneously started. The stopwatch is stopped when the 2 mL of fluid is taken into the material. A second insult of 2 mL is then dispensed and timed. The second insult is followed by a third insult, this time consisting of 1 mL, which is also timed. This results in a total of 5 mL and three timed insults. Wait approximately 60 seconds from intake of the third insult before placing a pre-weighed blotter paper onto the 20 mL of material and applying a 0.5 psi pressure for 60 seconds. After 60 seconds, the blotter paper is reweighed and the fluid, in grams, that has been absorbed by the blotter paper is considered the amount of rewet. Testing is typically conducted under TAPPI Standard Conditions.

Equipment and Materials

Harvard Apparatus Programmable Syringe Pump, Model No. 44, commercially available from Harvard Apparatus, South Natick, Mass. 01760 USA.

The fluid in this instance, by way of example only and not by way of limitation, is an artificial menses (simulant), disclosed in U.S. Pat. No. 5,883,231, issued Mar. 16, 1999, to Achter et al., the disclosure of which is hereby incorporated herein by reference to the extent that said disclosure is consistent (i.e., not contradictory) with the present specification. The simulant disclosed and claimed in U.S. Pat. No. 5,883,231 is commercially available from Cocalico Biologicals, Inc., 449 Stevens Rd., P.O. Box 265, Reamstown, Pa. 17567 USA.

Disposable plastic weighing boats commercially available from NCL of Wisconsin, Inc., Birnamwood, Wis. 54414 USA, part number W-D 80055.

60 cc disposable syringe, commercially available from Becton Dickinson, Franklin Lakes, N.J. 07417 USA; Tygon tubing, size 16 with 0.12" inner diameter, part number 6409-16, commercially available from Cole-Parmer Instrument Company, Chicago, Ill. 60648 USA; and 1/8" outer diameter hose, barb size, part number R-3603 and also commercially available from Cole-Parmer Instrument Company.

5.5 cm blotter paper, commercially available from VWR Scientific Products, 1145 Conwell Ave., Willard, Ohio 44890 USA, catalogue number 28310-015.

Weight, made by taking a 100 mL Pyrex beaker and filling it with any suitable substance to 717.5 grams to obtain a 0.5 psi loading.

Balance, readable to 0.001 g (Note: standards should be NIST traceable and should be recertified at a frequency adequate to assure accuracy).

Stopwatch, readable to 0.1 s (Note: stopwatch should be NIST traceable).

Graduated cylinder readable to 20 mL.

Clear acrylic plate (of a size sufficient to be supported on top of a disposable plastic weighing boat) with a hole drilled approximately in the center thereof for insertion of the Tygon tubing.

Specimen Preparation

The simulant is removed from a refrigeration unit, placed on a rotator and then gently rotated for approximately 30 minutes to thoroughly mix the contents and bring the simulant to room temperature.

The graduated cylinder is placed onto the balance and the weight tared. 20 mL of material is introduced into the graduated cylinder. The graduated cylinder is removed from the balance. The bottom of the graduated cylinder is gently tapped on the top of the lab bench or similar hardened surface approximately 10 times to induce settling. Visual inspection is made to ensure that there is 20 mL of material in the graduated cylinder. The 20 mL of material is poured into a weighing boat and the material is gently leveled.

The Harvard Syringe Pump is set to the Program Mode. The Infuse Rate is set to 12 mL/min. with the Target Volume set to 2 mL. Diameter is set to the correct syringe size. The Harvard Syringe Pump is filled with approximately 60 mL of simulant.

The steps of the testing method are as follows:
1. One end of the Tygon tubing is inserted through the hole in the acrylic plate.
2. The acrylic plate is placed over a weighing boat containing 20 mL of absorbent material. The Tygon tubing should be placed approximately over the center of the material.
3. Simultaneously start the stopwatch and begin dispensing the first 2 mL insult of simulant.
4. Stop the stopwatch when the simulant is taken in by the material. The reading on the stopwatch is recorded as "Insult 1" in seconds. In the event that the simulant is not taken in by the material being tested (i.e., the simulant sits on the top of the material) within five minutes, stop the test and record 300+seconds.
5. Simultaneously start the stopwatch and begin dispensing the second 2 mL insult of simulant.
6. Stop the stopwatch when the simulant is taken in by the material. The reading on the stopwatch is recorded as "Insult 2" in seconds. In the event that the simulant is not taken in by the material being tested (i.e., the simulant sits on the top of the material) within five minutes, stop the test and record 300+seconds.
7. Simultaneously start the stopwatch and begin dispensing the simulant. In this instance, however, the Harvard Syringe Pump is halted after 1 mL of simulant has been dispensed.
8. Stop the stopwatch when the 1 mL of simulant is taken in by the material.

The reading on the stop watch is recorded as "Insult 3" in seconds. Once again, should the simulant not be taken in by the material being tested (i.e., the simulant sits on the top of the material) within five minutes, stop the test and record 300+seconds.

9. Wait 60 seconds after the third insult is taken in by the material.
10. Weigh two pieces of blotter paper and record this weight as "BP Dry."
11. At the end of the 60 seconds noted in step 9, gently place the blotter paper on the material and then gently place the 0.5 psi weight onto the blotter paper and start the stopwatch.
12. After 60 seconds, remove the weight and reweigh the blotter paper. This weight of the blotter paper is recorded as "BP Wet."

Steps 3 through 12 outlined above are repeated until the simulant is no longer taken in by the material (i.e., the simulant sits on the top of the material and is not taken in within five minutes).

The results of the rewet portion of the test method are recorded in grams and calculated as follows:

(BP Wet)−(BP Dry)=Rewet

Method for Determining Retention Capacity

As used herein, the Method for Determining Retention Capacity measures the amount of test fluid that a sample of material retains after a centrifugal force has been applied. The amount of fluid retained is calculated as a gram per gram retention. The test is typically conducted under TAPPI Standard Conditions. When the test fluid is a complex fluid, such as, for example, blood, menses, artificial menses (simulant), loose passages, nasal discharges and the like, the retention capacity of a material is sometimes referred to as a complex fluid retention capacity (CFRC).

In general, testing according to this method is performed by placing a 0.5 g sample of material into a modified cylinder, exposing the sample of material to a desired fluid for 60 minutes and then placing the cylinders into a centrifuge to remove excess fluid. The results are calculated to obtain the grams of fluid retained per gram of sample of material.

Equipment and Materials

Artificial menses fluid (simulant), disclosed in U.S. Pat. No. 5,883,231, issued Mar. 16, 1999, to Achter et al. The simulant disclosed and claimed in U.S. Pat. No. 5,883,231 is commercially available from Cocalico Biologicals, Inc. 449 Stevens Rd., P.O. Box 265, Reamstown, Pa. 17567 USA.

Sorvall RT 6000D centrifuge, commercially available from Global Medical Instrumentation, Inc., 3874 Bridgewater Dr., St. Paul, Minn. 55123 USA.

Four 200 mL, screw top centrifuge bottles, commercially available from International Equipment Co., 300 Second Ave., Needham Heights, Ma. 02494 USA.

Balance, readable to 0.001 g (Note: standards should be NIST traceable and should be recertified at a frequency adequate to assure accuracy).

Four 50 mL Pyrex beakers.

Lab timer, 60 minute capacity, readable to one second, commercially available from VWR Scientific Products, 1145 Conwell Ave., Willard, Ohio 44890 USA.

Four modified Lexan cylinders, 9 cm high, 3.1 cm ID, 4.8 cm OD, with a 300 holes/in$^2$ screen attached to the bottom.

U.S. standard 30 and 50 screen sieves, 8 inch diameter, 2 inch height, commercially available from VWR Scientific Products, 1145 Conwell Ave., Willard, Ohio 44890 USA, catalogue numbers 57334-456 and 57334-464, respectively.

Stainless steel screen, 4 holes per inch or enough open space to allow simulant to drain.

Specimen Preparation

Prepare the sample of material by using the U.S. standard 30 and 50 screen sieves to fractionate a sample to the 300 to 600 micron size. Store the fractionated sample of material in a sealed substantially airtight container for use when the sample or samples of material will be prepared. The modified cylinder is placed on the balance and the weight tared. Place 0.5 g±0.005 g of the fractionated sample into one of the modified cylinders. Record this weight as Sample Weight. The modified cylinder containing the sample of material is weighed and this weight is recorded as Dry Cylinder Weight. Additional samples of material are placed in the three remaining modified cylinders according to the foregoing steps.

The simulant is removed from a refrigeration unit, placed on a rotator and then gently rotated for approximately 30 minutes to thoroughly mix the contents and bring the simulant to room temperature.

The steps of the testing method are as follows:

1. Approximately 10 mL of simulant are placed into a 50 mL Pyrex beaker.
2. A modified cylinder containing the sample of material is placed into the 50 mL Pyrex beaker.
3. Approximately 15 mL of simulant are poured into the modified cylinder. This ensures that the sample of material has access to the simulant from both above and below.
4. Repeat step 1 through 3 as necessary for any desired additional sample of material.
5. After step 4 has been completed, the timer is set for 60 minutes and started.
6. After 60 minutes have elapsed, the modified cylinders are removed from the Pyrex beakers and placed on the stainless steel screen for 60 seconds.
7. After 60 seconds, the modified cylinders are removed from the stainless steel screen and placed in the 200 mL centrifuge bottles.
8. The centrifuge bottles are placed in the centrifuge for 3 minutes at 1,200 rpm.
9. After 3 minutes, the modified cylinders are removed from the centrifuge bottles and the modified cylinders containing the samples of material are weighed. This weight is recorded as Wet Cylinder Weight.

The Complex Fluid Retention Capacity ("CFRC") of each sample of absorbent is then calculated according to the following formula:

$$\frac{[(\text{Wet Cylinder Weight} - \text{Dry Cylinder Weight}) - \text{Product Weight}]}{(\text{Product Weight})}$$

Where reported in any of the following examples, the Retention Capacities are an average of two samples (i.e., n=2).

EXAMPLES

The following Examples describe various embodiments of the invention. Other embodiments within the scope of the claims herein will be apparent to one skilled in the art from consideration of the specification or practice of the invention as disclosed herein. It is intended that the specification, together with the Examples, be considered exemplary only, with the scope and spirit of the invention being indicated by the claims which follow the Examples.

Example 1

This Example illustrates the preparation of fiber bundles using a BIVIS disperser (Model BC-45, commercially available from by Clextral Co., Firminy Cedex, France). Bahia Sul eucalyptus pulp sheets were fed to a pulper (Medium Consistency Pulper Model 01R, Cellwood Grubbens AB, Sweden) with the addition of dilution water to reach a consistency of approximately 6 percent. The pulp sheets were treated in the pulper for approximately 30 minutes. Runs were performed with and without a debonding agent.

For runs with debonding agent, the debonding agent was added approximately five minutes after the pulp sheets were fed into the pulper. At the end of pulping, the pulp was further diluted to a consistency of approximately 4.5 percent and pumped via a pulper dump pump over to a dump chest having an agitator running. The BIVIS dump tank transfer pump was set to be in the recirculating mode. A belt press (Continuous Belt Press, Model CPF 0.5 meter, P3, Andritz-Ruthner, Inc., Arlington, Tex. USA) was used to de-water the pulp. Once activated, the feed valve of the BIVIS dump tank transfer pump was opened and the recirculation valve was closed. The belt press was configured to provide a discharge mat approximately 2.5 cm thick. Discharge consistency was approximately 32 percent. The discharge mat was broken up by a break-up screw at the end of the belt press and then was transferred by the screw conveying system to the feed hopper of the BIVIS disperser.

The pulp was further disintegrated by the double feed screw system in the bottom of the feed hooper. The disintegrated pulp was fed to the BIVIS feed screw and directly into the BIVIS disperser. The internal configuration of the BIVIS disperser is a double, co-rotating, shaft disperser with interchangeable screw elements for transferring the pulp axially along the disperser. The screw elements utilized had half-moon slots (tackle 2). Periodically, along the length of the BIVIS disperser there are reverse-flighted screws to introduce backpressure to the pulp. Three working zones were used in this Example with each zone having the screw profile identified in TABLE 1 below. All screw elements were single flight.

TABLE 1

| BIVIS Zone | Element Number | Flight | Length (mm) | Pitch (mm) | Slot Width (mm) |
| --- | --- | --- | --- | --- | --- |
| Feed | 1 | Forward | 100 | +50 | 0 |
| Feed | 2 | Forward | 100 | +50 | 0 |
| 1 | 3 | Forward | 100 | +33 | 0 |
| 1 | 4 | Forward | 50 | +25 | 0 |
| 1 | 5 | Reverse | 50 | −15 | 6 |
| 2 | 6 | Forward | 100 | +33 | 0 |
| 2 | 7 | Forward | 50 | +25 | 0 |
| 2 | 8 | Reverse | 50 | −15 | 6 |
| 3 | 9 | Forward | 100 | +33 | 0 |
| 3 | 10 | Forward | 50 | +25 | 0 |
| 3 | 11 | Reverse | 50 | −15 | 6 |
| Discharge | 12 | Forward | 100 | +33 | 0 |
| Discharge | 13 | Forward | 100 | +33 | 0 |

Two extraction zones were used for all runs. Extraction plates were installed in Zones 1 an 2. Water and pulp fines were extracted from these zones.

For all samples, an attempt was made to control energy input to a low-to-intermediate level in one set of runs and to a higher energy input level for another set of runs. Temperature was recorded. Maximum temperature generally correlates directly to energy input, but maximum temperature tended to migrate toward Zone 1 as time progressed. Approximate ranges of these parameters are provided in TABLE 2 below.

TABLE 2

| Parameter | Range |
| --- | --- |
| Specific Energy (kW-h/T) | 90 to 218 |
| Outlet Consistency (%) | 46 to 55 |
| Maximum Temperature (° C.) | 99 to 116 |

The debonding agent utilized in this Example was MacKernium 516Q-60 (a tertiary amine, commercially available from MacIntyre Group Ltd., 24601 Governor's Highway, University Park, Ill. 60466 USA) added at a dose of 2.78 kg (6.15 pounds) per metric ton.

The fibrous structures prepared according to this Example were then oven dried overnight at approximately 43° C.

Example 2

This Example illustrates the preparation of fiber bundles using a Maule disperser (GR II, Ing. S. Maule & C. S.p.A., Torino, Italy). Approximately 800 kg of Bahia Sul bleached eucalyptus kraft pulp were fed to a high consistency pulper (Model ST-C-W, Voith-Sulzer PaperTech, formerly Sulzer Escher-Wyss Gmbh, Ravensburg, West Germany) with the addition of dilution water to reach a consistency of between about 12 and 15 percent. The pulp was treated in the pulper for approximately 30 minutes. At the end of pulping, the pulp was further diluted to a consistency of approximately 4 percent and pumped via a pulper dump pump over to a dump chest having an agitator running. The pulp was then pumped at a consistency of approximately 4 percent to a washer (Double Nip Thickener, Model 200, Black Clawson Co., Middletown, Ohio USA) where it was de-watered to a consistency of approximately 12 percent and fed via a screw conveyor to the headbox of a belt press (Continuous Belt Press, Model CPF 0.5 meter, P3, Andritz-Ruthner, Inc., Arlington, Tex. USA).

The pulp was discharged from the belt press at a consistency of about 35 percent to a break-up screw at the end of the belt press and then transferred to the Maule disperser by a heating screw, to raise the inlet temperature to approximately 80° C. The Maule outlet temperature was approximately 100° C. Targeted energy input into the disperser was approximately 98 kW-h/ton (5.5 horsepower-days per ton).

Another run was performed using the procedure set forth in this Example with the following exception: the outlet door to the disperser was closed and the disperser was operated with a rotor speed of about 48 rpm for approximately 10 minutes. This resulted in a higher energy input to the pulp, causing the fiber bundles to be smaller with fewer fibers projecting from the surface of the fiber bundles.

Example 3

Bleached kraft eucalyptus pulp from Aracruz, Inc. was fed to a high consistency pulper (Model ST-C-W, Voith-Sulzer PaperTech) with the addition of dilution water to reach a consistency of between about 12 and about 15 percent. The pulp was treated in the pulper for approximately 30 minutes. Runs were performed with and without a debonding agent. For runs with debonding agent, the debonding agent (in this instance MacKernium 516Q-60) was added in an amount equivalent to about 2.78 kg per metric ton approximately 10 minutes after the pulp was fed into the high consistency pulper. At the end of pulping, the pulp was further diluted to a consistency of approximately 4 percent and pumped via a pulper dump pump over to a dump chest having an agitator running. The pulp was then pumped at a consistency of approximately 4 percent to a washer (Double Nip Thickener, Model 200, Black Clawson Co. Middletown, Ohio USA) where it was de-watered to a consistency of approximately 12 percent and fed via a screw conveyor to a headbox of a belt press (Continuous Belt Press, Model CPF 0.5 meter, P3, Andritz-Ruthner, Inc., Arlington, Tex. USA). The pulp was discharged from the belt press at a consistency of about 35 percent to a break-up screw at the end of the belt press and then transferred to a Maule disperser (GR II, Ing. S. Maule & C. S.p.A., Torino, Italy) by a heating screw, to raise the inlet temperature to approximately 80° C. Targeted energy input into the disperser was approximately 98 kW-h/ton (approximately 5.5 horsepower-days/ton). The Maule outlet temperature was approximately 100° C. The fibrous bundles were oven dried over night at approximately 43° C. The fibrous bundles were sieved to different size particles as identified in Table 3 below. The percentage of yield at the different particle sizes indicates a significant difference between fibrous structures including a debonding agent (i.e., debonded) when compared to otherwise substantially similar fibrous structures that do not comprise the debonding agent (i.e., non-debonded). Surprisingly, the percent yield for the particle size between about 300 to about 600 microns was much higher when a debonding agent was added to the pulp. Particle size distribution and percentage yield for fibrous structures of this Example are provided in Table 3 below.

TABLE 3

| Screen Number | Particle Size (microns) | Percent per Screen of Debonded Absorbent Fibrous Structures (n = 4) | Percent per Screen of Non-Debonded Absorbent Fibrous Structures (n = 4) |
|---|---|---|---|
| 20 | >850 | 41 | 63 |
| 30 | 600–850 | 25 | 20 |
| 50 | 300–600 | 35 | 12 |
| Pan | <300 | 3 | 1 |

Table 4 illustrates the complex fluid retention capacities of both debonded and non-debonded fibrous structures prepared in accordance with this Example as measured according to the Method for Determining Retention Capacity provided above. The addition of a debonding agent increased the complex fluid retention capacity (CFRC), a surprising result given that a desirable debonding agent is usually characterized as being hydrophobic. The control codes were non-debonded Weyerhaeuser NB416 pulp and debonded Weyerhaeuser NF405 pulp. Pulp-based materials having a debonding agent typically have a reduced complex fluid retention capacity.

TABLE 4

| Screen Number | Particle Size (microns) | CFRC of Debonded Structures (g/g) | CFRC of Non-Debonded Structures (g/g) | Increase in CFRC of Debonded v. Non-Debonded (%) |
|---|---|---|---|---|
| As is | Varies | 2.3 | 1.4 | 40 |
| 20 | >850 | 2.6 | 1.6 | 38 |
| 30 | 600–850 | 2.0 | 1.6 | 20 |
| 50 | 300–600 | 2.3 | 1.7 | 26 |
| NB416 | — | — | 5.7 | — |
| NF405 | — | 3.9 | — | — |

As illustrated in TABLE 4, the fibrous structures prepared according to the present invention exhibited a complex fluid retention capacity that is at least about 20; alternatively, at least about 26; alternatively, at least about 38; and finally, alternatively, at least about 40 percent greater than the complex fluid retention capacity exhibited by an otherwise substantially similar fibrous structure that does not include a debonding agent.

TABLES 5 through 9 illustrate the intake rate and rewet of the fibrous structures prepared according to the present invention. When determining intake rate and rewet, the third insult was 1 mL, while the first two insults used 2 mL of fluid. The following tables also illustrate that, on average, the non-debonded fiber bundles had higher rewet values than did the debonded fibrous structures. An unsieved (i.e., "as is") sample of the debonded fibrous structures (Sample J) was compared to an unsieved sample of non-debonded fiber bundles (Sample K). The results of this comparison are provided in Table 5.

TABLE 5

|  | Sample J | Sample K |
|---|---|---|
| Insult 1 (s) | 29.6 | 26.5 |
| Insult 2 (s) | 29.6 | 29.3 |
| Insult 3 (s) | 17.3 | 15.1 |
| Rewet (g) | 0.57 | 0.67 |

A sieved (20 mesh) sample of the debonded fibrous structures (Sample L) was compared to a sieved (20 mesh) sample of non-debonded fiber bundles (Sample M). The results of this comparison are provided in Table 6.

TABLE 6

|  | Sample L | Sample M |
|---|---|---|
| Insult 1 (s) | 28.0 | 30.3 |
| Insult 2 (s) | 28.6 | 30.7 |
| Insult 3 (s) | 14.9 | 18.8 |
| Rewet (g) | 0.67 | 0.77 |

A sieved (30 mesh) sample of the debonded fibrous structures (Sample N) was compared to a sieved (30 mesh) sample of non-debonded fiber bundles (Sample O). The results of this comparison are provided in Table 7.

TABLE 7

|  | Sample N | Sample O |
|---|---|---|
| Insult 1 (s) | 28.1 | 28.0 |
| Insult 2 (s) | 30.5 | 29.4 |
| Insult 3 (s) | 17.7 | 15.9 |
| Rewet (g) | 0.85 | 0.59 |

A sieved (50 mesh) sample of the debonded fibrous structures (Sample P) was compared to a sieved (50 mesh) sample of non-debonded fiber bundles (Sample Q). The results of this comparison are provided in Table 8.

TABLE 8

|  | Sample P | Sample Q |
|---|---|---|
| Insult 1 (s) | 28.8 | 28.5 |
| Insult 2 (s) | 30.1 | 31.4 |
| Insult 3 (s) | 16.9 | 18.1 |
| Rewet (g) | 0.55 | 0.77 |

A sieved (30–50 mesh) sample of the debonded fibrous structures (Sample R) was compared to a sieved (30–50 mesh) sample of non-debonded fiber bundles (Sample S). The results of this comparison are provided in Table 9.

TABLE 9

|  | Sample R | Sample S |
|---|---|---|
| Insult 1 (s) | 29.0 | 29.2 |
| Insult 2 (s) | 33.2 | 30.6 |
| Insult 3 (s) | 19.6 | 16.5 |
| Rewet (g) | 0.92 | 0.62 |

Example 4

This Example illustrates that an increase in the debonding agent did not significantly affect the complex fluid retention capacity (CFRC) of the fibrous structures. The fibrous structures of this Example were prepared according to the method disclosed in Example 1 above. Table 10 identifies the complex fluid retention capacity (CFRC) values for these absorbent fibrous structures having a debonding agent (MacKernium 516Q-60) applied at three different levels. The absorbent fibrous bundles were oven dried over night at approximately 43° C. An increase in debonding agent did not appear to significantly reduce the retention capacity of the fibrous bundles.

TABLE 10

| Particle Size (microns) | Amount of Debonding Agent Added (kg per metric ton of pulp) | CFRC (g/g) |
|---|---|---|
| 300–850 | 0.68 | 1.6 |
| 300–850 | 2.78 | 1.2 |
| 300–850 | 4.54 | 1.6 |

Control codes, non-debonded Weyerhaeuser NB416 pulp and debonded NF405 pulp, were similarly tested and resulted in CFRC values of 5.7 and 3.9 g/g, respectively. As expected, pulp-based materials with a debonding agent normally demonstrate reduced CRFC values.

Example 5

To quantitatively describe the interior structure of the absorbent fibrous structures, Back-Scattered Electron/High-Contrast (BSE/HICON) images of cross sectioned fibrous structures were acquired to quantify percent pore area. Eight to ten fibrous structures from each manufacturing code were linearly taped to an index card with double-sided tape. A second piece of double-sided tape was placed over the fibrous structures to encapsulate them. This assembly was plunged into liquid nitrogen and cut along the midline of the fibrous structure with a TEFLON-coated razor blade. The sectioned fibrous structures were thereafter allowed to reach room temperature before mounting to a SEM mount and sputter coating with 30 nm of gold. All sections were imaged at a 12 mm working distance on a JEOL 840 equipped with a solid-state, annular back-scattered electron detector. The SEM was operated at 10 kV with a condenser lens setting of 1 nA. Both secondary electron and compositional BSE images were recorded. The BSE images used for quantification were recorded on POLAROID Type 51 high-contrast film. Contrast and brightness were adjusted to a predetermined minimum/maximum waveform signal for each section to generate near-binary images. Data were obtained from cross-sectional BSE/HICON images using a Quantimet 600 IA System and the following custom-written QUIPS routine entitled "NITPORE1":

Routine Header:
  Number of fields: 1
  Standard Frames
  Results header:
    System and Version, Routine Name, Date and time, Calibration value
    User Name: "Dave Biggs"
    Specimen ID: " "
    Description: "Fiber Nit Internal Void Space (i.e., %Open Area of Cross-section)"
NAME: NITPORE1
PURPOSE: To measure internal space (% Area) of Fiber Nit Cross-sections
CONDITIONS: 20 mm adj. Nikon lens (f/4); SONY 3CCD vid.; ¼" glass cover plate; pole pos.=77.3 cm; Kreonite macroviewer
AUTHOR: D. G. Biggs
DATE: Nov. 15, 1999
COUNT=0
NUMFIELD=0
PERCAREA=0
POREAREA=0
TOTAREA=0
TOTCOUNT=0
TOTPERCAREA=0
READ IMAGE AND SAMPLE ENTRY
Enter Results Header
BEGIN:
Image Setup [PAUSE] (Camera 5, White 78.34, Black 100.00, Lamp 44.88)
Acquire (into Image0)
SET FRAMES AND DETECT VOID SPACE AREAS
Image frame (x 0, y 0, Width 736, Height 574)
Measure frame (x 36, y 35, Width 668, Height 537)
Detect (whiter than 110, from Image0 into Binary0 delineated)
IMAGE PROCESSING
Binary Edit [PAUSE] (Accept from Binary0 to Binary1, nib Fill, width 2)
Binary Amend (Close from Binary1 to Binary2, cycles 5, operator Disc, edge erode on)
Binary Identify (FillHoles from Binary2 to Binary3)
Binary Amend (Open from Binary3 to Binary4 cycles 2 operator Disc, edge erode on)
Binary Logical (C=A XOR B; C Binary5, A Binary1, B Binary4)
FIELD MEASUREMENTS AND HISTOGRAM
  MFLDIMAGE=4
Measure field (plane MFLDIMAGE, into FLDRESULTS (2) )
  Selected parameters: Area, Area%
TOTAREA=FLDRESULTS(1)
MFLDIMAGE=5
Measure field (plane MFLDIMAGE, into FLDRESULTS (4) )
  Selected parameters: Area, Count, Area%, Count/Area
POREAREA=FLDRESULTS(1)
PERCAREA=POREAREA/TOTAREA*100
TOTPERCAREA=totpercarea+percarea
COUNT=FLDRESULTS(4)

TOTCOUNT=TOTCOUNT+COUNT
NUMFIELD=NUMFIELD+1
Field Histogram#1 (Y Param Number, X Param PERCAREA, from 10. To 70., linear, 30 bins)
Display Field Histogram Results (#1, horizontal, differential, bins+graph (Y axis linear), statistics)
Data Window (740, 416, 540, 605)
INTERACTIVE DIALOGUE
PauseTest ("IF YOU WANT TO CONTINUE, ENTER '1'.")
Input (CONTINUE)
If (CONTINUE=1)
  Goto BEGIN
Endif
DATA OUTPUT
Set Print Position (8 mm, 12 mm)
Print Results Header
Print ("Total Number of Fields=", no tab follows)
Print (NUMFIELD, 0 digits after '.', no tab follows)
Print Line
Print ("Average Percent Open Area (%)=", no tab follows)
Print (TOTPERCAREA/NUMFIELD, 2 digits after '.', no tab follows)
Print Line
Print ("Pore Count/Area=", no tab follows)
Print (TOTCOUNT/(NUMFIELD*1000), 2 digits after '.', no tab follows)
Print Line
Print Line
Print ("COUNT VS. % FIELD AREA", tab follows)
Print Line
Print Field Histogram Results (#1, horizontal, differential, bins +graph (Y axis linear), statistics)
Set Image Position (left 94 mm, top 159 mm, right 181 mm, bottom 227 mm,
Aspect=Image Window,
  Caption:Bottom Centre, "EXAMPLE IMAGE")
Grey Util (Print Image0)
END The optical configuration for the analysis included a 20 mm adjustable NIKON lens (f/4), a SONY 3CCD video camera, a ¼" glass cover plate and a KREONITE macroviewer pole position of 77.3 cm. Data were accumulated over nine fields-of-view. Sample 5-M was prepared according to the method disclosed in Example 3 above, while sample 5-C was prepared according to the method disclosed in Example 1 above u sing MacKernium 516Q-60 as the debonding agent.

Interior structural characterization of the fibrous structures are summarized in Tables 11 through 13.

TABLE 11

| Sample Identification | Mean Percent Pore Area | Standard Deviation | Pore Count Per Unit Area |
|---|---|---|---|
| 5-M | 50.39 | 5.39 | 0.91 |
| 5-C | 19.10 | 3.27 | 0.92 |

TABLE 12

| Sample Identification | Area Wt. Pore Length (μm) | Standard Deviation |
|---|---|---|
| 5-M | 190.59 | 125.54 |
| 5-C | 49.41 | 36.04 |

TABLE 13

| Sample Identification | Pore Spacing (μm) | Standard Deviation |
|---|---|---|
| 5-M | 4.06 | 0.68 |
| 5-C | 10.63 | 1.36 |

Data revealed that there were measurable differences (based on 90% confidence) in percent pore area when comparing fibrous structures produced using the MAULE disperser to fibrous structures produced using the BIVIS disperser. Fibrous structures produced using the MAULE disperser (Sample 5-M and produced according to the method disclosed in Example 3 above) possessed over twice the amount of internal pore area than was found in fibrous structure produced using the BIVIS disperser (Sample 5-C and produced according to the method disclosed in Example 1 above). However, there were no statistically significant differences observed between fibrous structures produced using the same disperser. The area weighted pore lengths of fibrous structures produced on the BIVIS disperser were less that one-half the area weighted pore lengths of fibrous structures produced on the MAULE disperser. (Pore length data were area weighted to help account for the difference in contributions of large and very small pores.) Mean pore spacing of fibrous structures produced on the BIVIS disperser was over two times greater than for fibrous structures produced on the MAULE disperser. Pore counts per unit area were not observed to be significantly different between fibrous structures produced on either the BIVIS or MAULE dispersers.

Example 6

This Example serves to illustrate the flowability of the fibrous structures prepared according to the present invention. The equipment used in this Example was the AERO-FLOW Automated Powder Flowability Analyzer available from TSI Incorporated, 7 Pomeroy Lane, Amherst, Mass. 01002-2905 USA. The AERO-FLOW utilizes deterministic chaos theory to characterize the flow of a sample of fiber bundles by its avalanching behavior in a rotating disc. All samples described in this Example were prepared according to the method disclosed in Example 1 above. The fiber bundles were placed inside a disc or drum and slowly rotated. As the disc rotated, the fiber bundles rotated with the disc until the fiber bundles reached an unstable position. When this unstable position was reached, the fiber bundles avalanched down within the disc and again began to rotate along with the disc until they again reached a point of instability. The time to avalanche is a function of the fiber bundles' flowability. The AERO-FLOW detects the avalanches and determines the time interval between avalanches. In this Example, the AERO-FLOW was equipped with a standard drum that was rotated at a speed of approximately 90 rpm for 600 seconds. In each instance, sample size was 50 mL. The fiber bundles had an equivalent particle size of between about 300 and about 600 microns. Flowability results are reported in TABLE 14 below:

TABLE 14

| Sample No. | Debonder | Mean Time To Avalanche (s) | Scatter About Mean (s) |
|---|---|---|---|
| 6-W | None | 3.96 | 1.95 |
| 6-J | None | 3.78 | 1.88 |
| 6-C | Mackernium 516Q | 4.32 | 2.47 |
| 6-P | Mackernium 516Q | 3.97 | 2.09 |
| 6-V | Mackernium KP | 5.30 | 2.79 |
| 6-K | Mackernium KP | 4.42 | 2.22 |

Mean time to avalanche provides a flowability index of the sample's flow property. As illustrated in FIG. 8, the smaller the flowability index, the more flowable the sample. The results of this Example illustrate suitable fibrous structures having a flowability index of less than about 6; alternatively, between about 3 and about 6; and finally, alternatively, between about 3.5 and about 5.5. The scatter about the mean is an index of the sample's cohesivity. As illustrated in FIG. 9, the smaller the cohesivity index, the less cohesive the sample. The results of this Example illustrate suitable fibrous structures having a cohesivity index of less than about 3.

In view of the above, it will be seen that the several advantages of the invention are achieved and other advantageous results attained.

As various changes could be made in the above processes, absorbent structures and disposable absorbent articles without departing from the scope of the invention, it is intended that all matter contained in the above description and shown in the accompanying drawings shall be interpreted as illustrative and not in a limiting sense.

What is claimed is:

1. A method of making fibrous structures, the method comprising (a) forming an aqueous suspension of fibers having an inlet consistency of at least about 20 weight percent, (b) adding a debonding agent to the aqueous suspension and (c) subsequently passing the aqueous suspension through a disperser with an energy input of at least about 90 kW-h/T of dry fiber to form fibrous structures that are extruded from the disperser, wherein the fibrous structures exhibit a complex fluid retention capacity that is at least about 20 percent greater than the complex fluid retention capacity exhibited by an otherwise substantially similar fibrous structure that does not include a debonding agent.

2. The method of claim 1, wherein the disperser has a volume-to-working surface area ratio of at least about 1 centimeter.

3. The method of claim 1, wherein the disperser has a volume-to-working surface area ratio of at least about 3 centimeters.

4. The method of claim 1, wherein the disperser has a volume-to-working surface area ratio of about 5 to about 10 centimeters.

5. The method of claim 1, wherein the inlet consistency is from about 20 to about 50 dry weight percent.

6. The method of claim 1, wherein the inlet consistency is from about 25 to about 45 dry weight percent.

7. The method of claim 1, wherein the inlet consistency is from about 30 to about 40 dry weight percent.

8. The method of claim 1, wherein the fibrous structures are dried.

9. A method of making fibrous structures, the method comprising (a) forming an aqueous suspension of fibers having an inlet consistency of at least about 20 weight percent, (b) passing the aqueous suspension through a disperser with an energy input of at least about 90 kW-h/T of dry fiber to form fiber bundles that are extruded from the disperser and (c) adding a debonding agent to the extruded fiber bundles to form fibrous structures, wherein the fibrous structures exhibit a complex fluid retention capacity that is at least about 20 percent greater than the complex fluid retention capacity exhibited by an otherwise substantially similar fibrous structure that does not include a debonding agent.

10. The method of claim 9, wherein the disperser has a volume-to-working surface area ratio of at least about 1 centimeter.

11. The method of claim 9, wherein the disperser has a volume-to-working surface area ratio of at least about 3 centimeters.

12. The method of claim 9, wherein the disperser has a volume-to-working surface area ratio of about 5 to about 10 centimeters.

13. The method of claim 9, wherein the inlet consistency is from about 20 to about 50 dry weight percent.

14. The method of claim 9, wherein the inlet consistency is from about 25 to about 45 dry weight percent.

15. The method of claim 9, wherein the inlet consistency is from about 30 to about 40 dry weight percent.

16. The method of claim 9, wherein the fibrous structures are dried.

17. A method of making fibrous structures, the method comprising (a) forming an aqueous suspension of fibers having an inlet consistency of at least about 20 weight percent, (b) passing the aqueous suspension through a disperser with an energy input of at least about 90 kW-h/T of dry fiber and (c) adding a debonding agent to the aqueous suspension as it passes through the disperser to form fibrous structures that are extruded from the disperser, wherein the fibrous structures exhibit a complex fluid retention capacity that is at least about 20 percent greater than the complex fluid retention capacity exhibited by an otherwise substantially similar fibrous structure that does not include a debonding agent.

18. The method of claim 17, wherein the disperser has a volume-to-working surface area ratio of at least about 1 centimeter.

19. The method of claim 17, wherein the disperser has a volume-to-working surface area ratio of at least about 3 centimeters.

20. The method of claim 17, wherein the disperser has a volume-to-working surface area ratio of about 5 to about 10 centimeters.

21. The method of claim 17, wherein the inlet consistency is from about 20 to about 50 dry weight percent.

22. The method of claim 17, wherein the inlet consistency is from about 25 to about 45 dry weight percent.

23. The method of claim 17, wherein the inlet consistency is from about 30 to about 40 dry weight percent.

24. The method of claim 17, wherein the fibrous structures are dried.

25. A method of making fibrous structures, the method comprising (a) forming an aqueous suspension of fibers having an inlet consistency of at least about 20 weight percent, (b) passing the aqueous suspension through a disperser with an energy input of at least about 90 kW-h/T of dry fiber to form fiber bundles that are extruded from the disperser, (c) drying the extruded fiber bundles and (d) subsequently adding a debonding agent to the extruded fiber bundles to form fibrous structures, wherein the fibrous structures exhibit a complex fluid retention capacity that is at least about 20 percent greater than the complex fluid retention capacity exhibited by an otherwise substantially similar fibrous structure that does not include a debonding agent.

26. The method of claim 25, wherein the disperser has a volume-to-working surface area ratio of at least about 1 centimeter.

27. The method of claim 25, wherein the disperser has a volume-to-working surface area ratio of at least about 3 centimeters.

28. The method of claim 25, wherein the disperser has a volume-to-working surface area ratio of about 5 to about 10 centimeters.

29. The method of claim 25, wherein the inlet consistency is from about 20 to about 50 dry weight percent.

30. The method of claim 25, wherein the inlet consistency is from about 25 to about 45 dry weight percent.

31. The method of claim 45, wherein the inlet consistency is from about 30 to about 40 dry weight percent.

* * * * *